United States Patent [19]

Tyers

[11] Patent Number: 4,847,281

[45] Date of Patent: Jul. 11, 1989

[54] METHOD OF MEDICAL TREATMENT OF ADDICTION

[75] Inventor: Michael B. Tyers, Ware, England

[73] Assignee: Glaxo Group Limited, London, England

[21] Appl. No.: 123,369

[22] Filed: Nov. 20, 1987

[30] Foreign Application Priority Data

Nov. 21, 1986 [GB] United Kingdom ............... 8627909

[51] Int. Cl.⁴ .......................................... A61K 31/415
[52] U.S. Cl. .................................. 514/397; 514/810; 514/812; 514/813
[58] Field of Search ............... 514/397, 810, 812, 813

[56] References Cited

FOREIGN PATENT DOCUMENTS 2153821A 8/1985 United Kingdom.

Primary Examiner—Stanley J. Friedman
Attorney, Agent, or Firm—Bacon & Thomas

[57] ABSTRACT

The invention relates to the use of 1,2,3,9-tetrahydro-9-methyl-3-[(2-methyl-1H-imidazol-1-yl)methyl]-4H-carbazol-4-one and physiologically acceptable salts and solvates thereof in the relief or prevention of a withdrawal syndrome resulting from addiction to a drug or substance of abuse and/or for the suppression of dependence on drugs or substances of abuse.

11 Claims, No Drawings

METHOD OF MEDICAL TREATMENT OF ADDICTION

This invention relates to a new medical use for a heterocyclic compound and pharmaceutical compositions containing it. In particular it relates to the use of 1,2,3,9-tetrahydro-9-methyl-3-[(2-methyl-1H-imidazol-1-yl)methyl]-4H-carbazol-4-one and the physiologically acceptable salts and solvates thereof in the treatment of subjects addicted, recovering from addiction, or liable to become addicted, to drugs or substances of abuse.

The aforementioned compound may be represented by the formula (I):

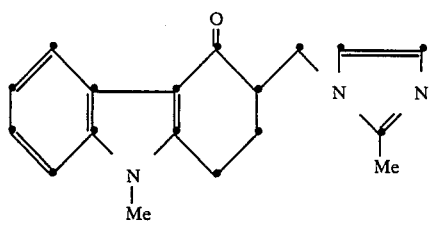

and is disclosed in UK Patent Specification No. 2153821A.

Suitable physiologically acceptable salts of the compound of formula (I) include acid addition salts formed with organic or inorganic acids for example, hydrochlorides, hydrobromides, sulphates, phosphates, citrates, fumarates and maleates. The solvates may, for example, be hydrates.

The aforementioned specification also discloses physiologically acceptable equivalents of the compound of formula (I), i.e. physiologically acceptable compounds which are converted in vivo into the parent compound of formula (I).

The compound of formula (I) is described in the aforementioned specification as a potent and selective antagonist of 5-hydroxytryptamine (5-HT) at 'neuronal' 5-HT receptors of the type located on terminals of primary afferent nerves. Receptors of this type are now designated as $5-HT_3$ receptors and are also present in the central nervous system. 5-HT occurs widely in the neuronal pathways in the central nervous system and disturbance of these 5HT containing pathways is known to alter behavioural syndromes such as mood, psychomotor activity, appetite and memory.

The compound is described as being of use in the treatment of a human or animal subject suffering from a condition caused by a disturbance of neuronal 5-HT function, for example in the treatment of a human subject suffering from migraine pain or a psychotic disorder such as schizophrenia. It is also stated that the compound may be useful in the treatment of conditions such as anxiety, obesity and mania.

We have now found that the compound of formula (I) may be used in the treatment of subjects addicted, recovering from addiction, or liable to become addicted, to drugs or substances of abuse.

Repeated administration to a subject of certain drugs such as opiates (e.g. morphine), cocaine or benzodiazepines (e.g. diazepam, chlordiazepoxide or lorazepam), or substances of abuse such as alcohol or nicotine (e.g., smoking) can lead to physical and/or phychological dependence upon that drug or substance. When the drug or substance of abuse is withdrawn from a dependent subject, the subject develops certain symptoms, such as aggressive behaviour, agitation, and intense craving for the drug or substance of abuse. These symptoms may be collectively described as a withdrawal or abstinence sydrome.

It has now been shown that administration of the compound of formula (I) can prevent, alleviate or reverse this withdrawal syndrome. The compound is therefore of use for the prevention or relief of a withdrawal syndrome resulting from addiction to drugs or substances of abuse.

It has also been shown that the compound of formula (I) suppresses dependence on drugs or substances of abuse. The compound is therefore also of use in reducing the craving for a drug or substance of abuse after addiction to that drug or substance, and can therefore be used for maintainence therapy during remission from addition to drugs or substances of abuse. The compound may also be used for prophylactic treatment of subjects liable to become dependent on drugs or substances of abuse.

The effectiveness of the compound of formula (I) in the treatment of a withdrawal syndome resulting from addiction to a drug or substance og abuse, and for the suppression of dependence on a drug or substance of abuse has been demonstrated in animals using, for example, the rat social interaction test, the light/dark exploration test in mice, a marmoset behavioural test and the drinkometer alcohol consumption test in rats.

Accordingly the invention provides a method of treatment for the relief or prevention of a withdrawal syndrome resulting from addiction to a drug or substance of abuse and/or for the suppression of dependence on drugs or substances of abuse, which comprises administering to a human or animal subject an effective amount of the compound of formula (I) or a physiologically acceptable salt or solvate thereof.

A preferred form of the compound of formula (I) is the hydrochloride, particularly in the hydrated form (e.g. the dihydrate).

In a further aspect, the invention provides a pharmaceutical composition which comprises an effective amount of the compound of formula (I) or a physiologically acceptable salt or solvate (e.g. hydrate) thereof, for use in human or veterinary medicine, for the relief or prevention of a withdrawal syndrome resulting from addiction to a drug or substance of abuse and/or for the suppression of dependence on drugs or substances of abuse.

In a yet further aspect, the invention provides for the use of the compound of formula (I) or a physiologically acceptable salt or solvate thereof, for the manufacture of a medicament for the relief or prevention of a withdrawal syndrome resulting from addiction to a drug or substance of abuse and/or for the suppression of dependence on drugs or substances of abuse.

Pharmaceutical compositions for use in accordance with the present invention may be formulated in conventional manner using one or more physiologically acceptable carriers or excipients.

Thus the compound of formula (I) and its physiologically acceptable salts and solvates may be formulated for oral, buccal, parenteral, rectal or transdermal administration or in a form suitable for administration by inhalation of insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compound of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compound of formula (I) may also be formulated in rectal compositions such as suppositories or retention enemas, e.g. containing conventional suppository bases such as cocoa butter or other glycerides.

In addition to the formulations described previously, the compound may also be formulated as a depot preparation. Such long acting formulations may be administered by implantation (for example subcutaneously, transcutaneously or intramuscularly) or by intramuscular injection. Thus, for example, the compound of formula (I) may be formulated with suitable polymeric or hydrophobic materials (for example as an emulsion in an acceptable oil) or ion exchange resins, or as sparingly soluble derivatives, for example, as a sparingly soluble salt.

A purposed dose of the compound of the invention for administration in man (of approximately 70 kg body weight) is 0.05 to 20 mg, preferably 0.1 to 10 mg of the active ingredient per unit dose, expressed as the weight of free base. The unit dose may be administered, for example 1 to 4 times per day. The dose will depend on the route of administration. It will be appreciated that it may be necessary to make routine variations to the dosage depending on the age and weight of the patient as well as the severity of the condition to be treated.

The compound of formula (I) may be prepared by the processes described in UK Patent Specification No. 2153821A.

The following examples illustrate the preparation of the compound of formula (I). Temperatures are in °C. Where indicated, solutions were dried over $Na_2SO_4$ and solids were dried in vacuo over $P_2O_5$ at 50° overnight.

EXAMPLE 1

1,2,3,9-Tetrahydro-9-methyl-3-[(2-methyl-1H-imidazol-1-yl)methyl]-4H-carbazol-4-one hydrochloride A solution of 2,3,4,9-tetrahydro-N,N,N,9-tetramethyl-4-oxo-1H-carbazole-3-methanaminium iodide (2.0 g) and 2-methylimidazole (5.0 g) in dry dimethylformamide (30 ml) was stirred, under nitrogen, at 95° for 16.75 h and then allowed to cool. The solid that crystallised was filtered off, washed with ice-cold, dry dimethylformamide (3×2 ml) and dry ether (2×10 ml) and then dried. The resulting solid (0.60 g) was suspended in a mixture of absolute ethanol (30 ml) and ethanolic hydrogen chloride (1 ml), and warmed gently to obtain a solution, which was filtered whilst warm. The filtrate was then diluted with dry ether to deposit a solid (0.6 g) which was recrystallised from absolute ethanol to give the title compound as a solid (0.27 g) m.p. 186°–187°.

EXAMPLE 2

1,2,3,9-Tetrahydro-9-methyl-3-[2-methyl-1H-imidazol-1-yl)methyl]-4H-carbazol-4-one A solution of 3-[(dimethylamino)methyl]-1,2,3,9-tetrahydro-9-methyl-4H-carbazol-4-one hydrochloride (1.7 g) in water (17 ml) was treated with 2-methylimidazole (1.4 g) and then heated under reflux for 20 h. The cooled mixture was filtered and the residue washed with water (3×15 ml) to give a product (1.7 g) m.p. 221°–221.5°. This material was recrystallised from methanol to give the title compound (1.4 g) m.p. 231°–232°.

EXAMPLE 3

1,2,3,9-Tetrahydro-9-methyl-3-[(2-methyl-1H-imidazol-1-yl)methyl]-4H-carbazol-4-one hydrochloride dihydrate 1,2,3,9-Tetrahydro-9-methyl-3-[(2-methyl-1H-imidazol-1-yl)methyl]-4H-carbazol-4-one (18.3 g) in a hot mixture of isopropanol (90 ml) and water (18.3 ml) was treated with concentrated hydrochloric acid (6.25 ml). The hot mixture was filtered and the filtrate diluted with isopropanol (90 ml) and stirred at room temperature for 17 h, cooled to 2° and the solid filtered off (21.6 g). A sample (6 g) was recrystallized from a mixture of water (6 ml) and isopropanol (10 ml) to give the title compound as a white crystalline solid (6 g) m.p. 178.5°–179.5°.

Analysis Found: C,59.45;H,6.45;N,11.5. $C_{18}H_{19}N_3O \cdot HCl \cdot 2H_2O$ requires C,59.1;H,6.6;N,11.5%. Water assay Found: 10.23% $C_{18}H_{19}N_3O \cdot HCl \cdot 2H_2O$ requires 9.85%

The efficacy of the compound of formula (I) in the treatment of a withdrawal syndrome after addiction to a drug or substance of abuse, and for the suppression of dependence on a drug or substance of abuse has been demonstrated in the rat, mouse and marmoset using standard pharmacological tests for observing behavioural changes in animals, for example in the rat social interaction test, the light/dark exploration test in mice, a marmoset behavioural test and the 'drinkometer' alcohol consumption test in rats.

Test compound: 1,2,3,9-tetrahydro-9-methyl-3-[(2-methyl-1H-imidazol-1-yl)methyl]-4H-carbazol-4-one hydrochloride dihydrate.

RAT SOCIAL INTERACTION TEST

Animals

Male Hooded Lister rats (200–250 g), were housed 5 to a cage and kept in the laboratory environment for at least a week before testing. Rats paired in the test were taken from separate cages.

PROCEDURES AND RESULTS

The method was based on that described S. E. File, J. Neurosci. Meth., 1980, 2, 219–238. The test arena consisted of an open-topped bo, $62 \times 62 \times 33$ cm with a $7 \times 7$ matrix of infra-red photocell beams in the walls, 2.5 cm from the floor. The light intensity at the floor of the arena was 3.5 lux under low light conditions. Rats were exposed to the arena in pairs for 10 minutes on the day before the experiment. Rats were paired with different partners on the test day.

Drugs were tested by subjecting both members of a pair of rats to the same treatment at the pre-determined time before testing. Where a 45 minute pre-treatment time was used, the rats were placed singly in small cages immediately after dosing until they were tested. Where longer pre-treatment times were used, the rats were returned to their home cages after dosing and placed in the single cages 45 minutes before testing. All drugs were administered orally.

Testing involved placing each member of a pair of rats in opposite corners of the arena and then leaving them undisturbed for 10 minutes while recording their behaviour remotely on videotape. The behavioural assessments were made subsequently from the recordings. The time spent in social interaction was measured and expressed as a cumulative total for a 10 minute session. The behaviours that comprised social interaction were : following with contact, sniffing (but not sniffing of the hindquarters), crawling over and under, tumbling, boxing and grooming. Sniffing of the hindquarters was excluded because it was markedly influenced by the degree of urination and defaecation.

Thus, in the present experiment, rats (n=8 pairs) were dosed with diazepam, 40 mg/kg/day, for 7 days. Diazepam dosing was abruptly ceased and the rats were tested 24 h after the last dose under low light familiar conditions in the above described Social Interaction Test (A).

Upon abrupt cessation of dosing with diazepam and administration of RO15-1788, 10 mg/kg 45 min. before testing, the rats displayed an abstinence syndrome manifest as a reduction in social interaction when examined, under low light, familiar conditions (B). This abstinence syndrome was reversed by administration of the test compound, 0.01 mg/kg 45 min. before testing (C). Tests (B) and (C) were also conducted 24 h after the last dose of diazepam.

Treatment of the rats with the test compound, 0.01 mg/kg, alone, had no effect on social interaction under the low light familiar conditions.

|     | Treatment (mg/kg)                          | Mean Social Interaction(s) |
| --- | ------------------------------------------ | -------------------------- |
|     | Vehicle/Vehicle                            | $56.0 \pm 9.3$             |
| (A) | Diazepam/Vehicle 40                        | $44.7 \pm 4.0$             |
| (B) | Diazepam/RO15-1788 40   10                 | $11.0 \pm 1.7^{1,2}$       |
| (C) | Diazepam/RO15-1788 + Test Compound 40  10  0.01 | $38.3 \pm 6.7^{3}$    |

Results are means ±s.e.m. (standard error of the mean).
1 $p < 0.01$ vs vehicle/vehicle
2 $p < 0.01$ vs diazepam/vehicle
3 $p < 0.05$ vs diazepam/RO15-1788
Dunnett's t-test.

LIGHT/DARK EXPLORATION TEST IN MICE

Animals

Male albino BKW mice, 25–30 g, were housed 10 to a cage and allowed free access to food and water. They were kept on a reversed light cycle with the lights on between 22.00 h and 10.00 h.

PROCEDURE AND RESULTS

The method was based on that described by J. Crawley and F. K. Goodwin, Pharmacol. Biochem. and Behaviours, 1980, 13, 167–170.

The apparatus was an open-topped box, 45 cm long, 27 cm wide and 27 cm high, divided into a small (2/5) area and a large (3/5) area by a partition that extended 20 cm above the walls. There was a $7.5 \times 7.5$ cm opening in the partition at floor level. The small compartment was painted black and the large compartment white. The floor of each compartment was marked into 9 cm squares. The white compartment was illuminated by a 100W tungsten bulb 17 cm above the box and the black compartment by a similarly placed 60W red bulb. The laboratory was illuminated with red light.

All tests were performed between 13.00 h and 18.00 h. Each mouse was tested by placing it in the centre of the white area and allowing it to explore the novel environment for 5 minutes. Its behaviour was recorded on videotape and the behavioural analysis was performed subsequently from the recording. Five parameters were measured: the latency to entry into the dark compartments, the time spent in each area, the number of transitions between compartment, the number of lines crossed in each compartment and the number of rears in each compartment. Drugs were administered intraperitoneally.

Thus, in the present experiment, mice (n=5–10 per group) were treated with nicotine 0.1 mg/kg, twice daily for 14 days. Nicotine dosing was then abruptly ceased and the mice were tested 8 h after the last dose whereupon they displayed an abstinence syndrome manifest as an increased tendency to stay in the dark area (A). Administration of the test compound (0.001 mg/kg) at the same time as the last dose of nicotine resulted in the prevention of this abstinence syndrome as demonstrated when the mice were again tested 8 h after the last dose of nicotine (B).

|     | Treatment (mg/kg)    | Rears/5 min (light) | Rears/5 min (dark) |
| --- | -------------------- | ------------------- | ------------------ |
|     | Vehicle              | 30.0                | 33.0               |
| (A) | Nicotine withdrawal  | $10.0^{1}$          | $52.7^{1}$         |

| | Treatment (mg/kg) | Rears/5 min (light) | Rears/5 min (dark) |
|---|---|---|---|
| (B) | Nicotine withdrawal + Test compound 0.001 | 52.0[1,2] | 12.0[1,2] |

Results are means, s.e.m. less than 11.2%.
1 $p<0.01$ vs vehicle control
2 $p<0.01$ vs nicotine withdrawal
Dunnett's t-test.

MARMOSET BEHAVIOURAL TEST

Marmosets show natural aggressive and protective behaviours towards strangers such as a human observer. Such behaviours include vocalisation, posturing, anal scenting, and spending time on the cage front. Following chronic treatment with alcohol administered in the drinking water and then abruptly withdrawn, these behaviours are markedly exacerbated.

PROCEDURE AND RESULTS

Common marmosets (Callithrix jacchus), body weights 315±20 g, of both sexes were housed in single sex pairs. They were tested in their home cages. Only marmosets that responded consistently and reliably to confrontation by an observer (see below) were used in the experiments. It was essential to allow 1 or 2 days between test days and no marmoset was tested more than 3 times in a week. Marmosets were subjected to one test only on each test day.

Drugs were injected subcutaneously (dissolved or suspended in saline) except where otherwise stated, each member of the pair receiving the same treatment. 45 minutes after drug treatment, the marmosets were confronted by an observer standing 0.6m in front of the cage. Over a 2 minute period, the number of "aggressive" postures shown by one member of the pair was recorded: tail erect with exposure of genitals, slit stare facial expression, scenting and arch piloerect locomotion (marmoset moves to and fro along perch with back arched and full body piloerection) (M. F. Stevenson and T. B. Poole, Animal Behaviour, 1976, 24, 428-451). In the following 2 minute period, the amount of time spent on the wire cage front was recorded. Any overt behavioural changes were also noted. The response of one member of each of the other treated pairs of marmosets were assessed before returning to the second member of the first pair. At least 2 pairs of marmosets were tested on any one occasion. The intensity of response evoked in the marmosets varied between observers. Consequently, the experiments described here were performed by the same observer.

Thus, in the present experiment marmosets (n=4) were treated with alcohol (2% v/v in drinking water) for 30 days. Alcohol dosing was abruptly withdrawn, and the marmosets displayed an abstinence syndrome manifest as less time spent on the cage front and an increase in aggressive posturing (A). Administration of the test compound (0.01 mg/kg) twice daily following withdrawal from alcohol resulted in a marked attenuation of this abstinence syndrome or abolition when the marmosets were tested on the sixth post-withdrawal day.

Furthermore, on continuation of the treatment with the test compound, when the animals were given a free choice to consume drinking water which contained either alcohol or no alcohol, the marmosets preferred to abstain from further alcohol intake.

| | Treatment (mg/kg) | Aggressive Postures | Time at Cage Front(s) |
|---|---|---|---|
| | Vehicle | 9.0 | 29.4 |
| (A) | Alcohol withdrawal | 13.8[1] | 10.6[1] |
| (B) | Alcohol withdrawal + Test compound 0.01 | 3.0[1,2] | 77.6[1,2] |

Results are means, s.e.m. 5-25%.
1 $p<0.05$ vs control
2 $p<0.05$ vs alcohol withdrawal.
Dunnettps t-test.

The 'Drinkometer' Alcohol Consumption Test in Rats

Rats given free choice to drink either water containing 2% v/v alcohol or water will in time choose to drink alcohol solution. The alcohol consumed and characteristics of this consumption, such as drinking bouts, indicate that these animals can become dependent upon alcohol. In alcohol preferring animals, administration of the test compound twice daily in doses of up to 0.01 mg/kg subcutaneously, markedly reduced the amount of alcohol consumed over a 24 h period.

The following examples illustrate pharmaceutical formulations for use according to the invention, containing 1,2,3,9-tetrahydro-9-methyl-3-[(2-methyl-1H-imidazol-1-yl) methyl]-4H-carbazol-4-one hydrochloride dihydrate as the active ingredient (1.25 g of the hydrochloride dihydrate contains 1.00 g of the free base).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Tablet | Direct Compression mg/tablet |
|---|---|
| Active Ingredient | 4.688 |
| Calcium Hydrogen Phosphate BP* | 83.06 |
| Croscarmellose Sodium NF | 1.8 |
| Magnesium Stearate BP | 0.45 |
| Compression weight | 90.0 |

*of a grade suitable for direct compression.

The active ingredient is passed through a 60 mesh sieve, blended with the calcium hydrogen phosphate, croscarmellose sodium and arnesium stearate. The resultant mix is compressed into tablets using a Manesty F3 tablet machine fitted with 5.5 mm, flat bevelled edge punches.

| Sub-lingual Tablet | mg/tablet |
|---|---|
| Active Ingredient | 2.5 |
| Compressible Sugar NF | 62.0 |
| Magnesium Stearate BP | 0.5 |
| Compression Weight | 65.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| Wet Granulation Conventional Tablet | mg/tablet |
|---|---|
| Active Ingredient | 2.5 |
| Lactose BP | 151.0 |
| Starch BP | 30.0 |
| Pregelatinised Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| Sub-Lingual Tablet | mg/tablet |
|---|---|
| Active Ingredient | 2.5 |
| Mannitol BP | 56.5 |
| Hydroxypropylmethylcellulose | 5.0 |
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| CAPSULES | mg/tablet |
|---|---|
| Active Ingredient | 2.5 |
| *Starch 1500 | 96.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight an if necessary changing the capsule size to suit.

SYRUP

This may be either a sucrose or sucrose free presentation.

| A. Sucrose Syrup | mg/5 ml dose |
|---|---|
| Active Ingredient | 2.5 |
| Sucrose BP | 2750.0 |
| Glycerine BP | 500.0 |
| Buffer | |
| Flavour | |
| Colour | as required |
| Preservative | |

| A. Sucrose Syrup | mg/5 ml dose |
|---|---|
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 2.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

| INJECTION FOR INTRAVENOUS ADMINISTRATION | |
|---|---|
| | mg/ml |
| Active Ingredient | 0.80 |
| Citric Acid Monohydrate BP | 0.50 |
| Sodium Citrate BP | 0.25 |
| Sodium Chloride BP | 9.00 |
| Water for Injections USP to | 1.0 ml |

The citric acid monohydrate, active ingredient, sodium citrate and sodium chloride are dissolved in the major portion of the water for injections, the solution is made to volume and mixed thoroughly. After filtration, the solution is filled under air into ampoules which are sealed by fusion of the glass. The ampoules are sterilised by autoclaving for at least 15 minutes at 121°–124° C.

| SUPPOSITORY | |
|---|---|
| Active Ingredient | 5.0 mg |
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size suppository moulds.

I claim:

1. A method of treatment for the relief or prevention of a withdrawal syndrome resulting from addiction to a drug or substance or abuse and/or for the suppression of dependence on drugs or substances of abuse, which comprises administering to a human or animal subject suffering from or liable to suffer from said withdrawal syndrome and/or dependent on a drug or substance of abuse an effective amount of 1,2,3,9-tetrahydro-9-methyl-3-[2-methyl-1H-imidazol-1-yl)methyl]-4H-carbazol-4-one or a physiologically acceptable salt or solvate thereof.

2. A method according to claim 1 wherein said 1,2,3,9-tetrahydro-9-methyl-3-[m2-ethyl-1H-imidazol-1-yl)methyl]-4H-carbazol-4-one is administered in the form of the hydrochloride dihydrate salt.

3. A method according to claim 1 wherein said 1,2,3,9-tetrahydro-9-methyl-3-[(2-methyl-1H-imidazol-1-yl)methyl]-4H-carbazol-4-one or a physiologically acceptable salt or solvate thereof is administered in a dose of 0.05 to 20 mg from 1 to 4 times per day, the dose being expressed as the weight of free base.

4. A method according to claim 3 wherein said dose is from 0.1 to 10 mg from 1 to 4 times per day.

5. A method according to claim 1 wherein said drug or substance of abuse is an opiate.

6. A method according to claim 1 wherein said drug or substance of abuse is cocaine.

7. A method according to claim 1 wherein said drug or substance of abuse is a benzodiazepine.

8. A method according to claim 1 wherein said drug or substance of abuse is alcohol.

9. A method according to claim 1 wherein said drug or substance of abuse is nicotine.

10. A method according to claim 1 wherein said 1,2,3,9-tetrahydro-9-methyl-3-[(2-methyl-1H-imidazol-1-yl)methyl]-4H-carbazol-4-one is administered orally, buccally, parenterally, rectally, or as a depot preparation.

11. A method according to claim 1 wherein said 1,2,3,9-tetrahydro-9-methyl-3-[2-methyl-1H-imidazol-1-yl)methyl]-4H-carbazol-4-one is administered in the form of a hydrochloride.

* * * * *

UNITED STATES PATENT AND TRADEMARK OFFICE
CERTIFICATE OF CORRECTION

PATENT NO. : 4,847,281

DATED : July 11, 1989

INVENTOR(S) : Michael B. TYERS

It is certified that error appears in the above-identified patent and that said Letters Patent is hereby corrected as shown below:

On the title page, in §56, under "References Cited," please insert the following:

--          US PATENT DOCUMENTS

| | | |
|---|---|---|
| 4,753,789 | 6/1988 | Tyers et al |
| 4,721,720 | 1/1988 | Wootton et al --; | under "FOREIGN PATENT DOCUMENTS," please insert the following:

| | | |
|---|---|---|
| -- 2193633A | 2/1988 | United Kingdom |
| 8502115A | 5/1985 | WO |
| 0272052 | 6/1988 | Europe |
| 2206788A | 1/1989 | United Kingdom |

OTHER DOCUMENTS

Mocchetti et al, *Eur. J. Pharm.*, 106, 1985, 427-430

Dellavedova et al., *Eur. J. Pharm.*, 85, 1982, 29-34

Yamada et al., *Arch. Int. Pharmacodyn.*, 262, 1988, 24-33

Snelgar et al., *J. Physiol.*, 314, 1981, 395-410

Herz et al., *Advances in Neurology*, 33, 1982, 81-88

Jhamandas, *Prog. Neuro-Psychopharmacol. Biol. Psychiat.*, 8, 1984, 565-570 --

UNITED STATES PATENT AND TRADEMARK OFFICE
CERTIFICATE OF CORRECTION

PATENT NO. : 4,847,281

DATED : July 11, 1989

INVENTOR(S) : Michael B. TYERS

It is certified that error appears in the above-identified patent and that said Letters Patent is hereby corrected as shown below:

Column 4, line 29, "methyl-3-[2" should read
-- methyl-3-[(2 --.

Column 10, line 60, "substance or abuse" should read
-- substance of abuse --.

Column 10, line 66, "yl-3-[2" should read
-- yl-3-[(2 --.

Column 11, line 2, "3-[m2-ethyl" should read
-- 3-[(2-methyl --.

Column 12, line 13, "3-[2-methyl" should read
-- 3-[(2-methyl --.

Signed and Sealed this

Twenty-fourth Day of July, 1990

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,847,281

DATED : July 11, 1989

INVENTOR(S) : Michael B. TYERS

It is certified that error appears in the above-identified patent and that said Letters Patent is hereby corrected as shown below:

On the title page, in §56, under "References Cited," please insert the following:

--              US PATENT DOCUMENTS 4,753,789    6/1988    Tyers et al 4,721,720    1/1988    Wootton et al --;

under "FOREIGN PATENT DOCUMENTS," please insert the following:

-- 2193633A    2/1988    United Kingdom 8502115A    5/1985    WO 0272052     6/1988    Europe 2206788A    1/1989    United Kingdom

OTHER DOCUMENTS

Mocchetti et al, *Eur. J. Pharm.*, 106, 1985, 427-430

Dellavedova et al., *Eur. J. Pharm.*, 85, 1982, 29-34

Yamada et al., *Arch. Int. Pharmacodyn.*, 262, 1983, 24-33

Snelgar et al., *J. Physiol.*, 314, 1981, 395-410

Herz et al., *Advances in Neurology*, 33, 1982, 81-88

Jhamandas, *Prog. Neuro-Psychopharmacol. Biol. Psychiat.*, 8, 1984, 565-570 --

UNITED STATES PATENT AND TRADEMARK OFFICE
CERTIFICATE OF CORRECTION

PATENT NO. : 4,847,281

DATED : July 11, 1989

INVENTOR(S) : Michael B. TYERS

It is certified that error appears in the above-identified patent and that said Letters Patent is hereby corrected as shown below:

Column 4, line 29, "methyl-3-[2" should read -- methyl-3-[(2 --.

Column 10, line 60, "substance or abuse" should read -- substance of abuse --.

Column 10, line 66, "yl-3-[2" should read -- yl-3-[(2 --.

Column 11, line 2, "3-[m2-ethyl" should read -- 3-[(2-methyl --.

Column 12, line 13, "3-[2-methyl" should read -- 3-[(2-methyl --.

UNITED STATES PATENT AND TRADEMARK OFFICE
CERTIFICATE OF CORRECTION

PATENT NO. : 4,847,281

DATED : July 11, 1989

INVENTOR(S) : Michael B. Tyers

It is certified that error appears in the above-identified patent and that said Letters Patent is hereby corrected as shown below:

This Certificate supersedes Certificate of Correction issued July 24, 1990.

Signed and Sealed this

Twenty-sixth Day of May, 1992

Attest:

DOUGLAS B. COMER

Attesting Officer

Acting Commissioner of Patents and Trademarks